(12) United States Patent
Sakai et al.

(10) Patent No.: US 9,823,467 B2
(45) Date of Patent: Nov. 21, 2017

(54) SCANNING TYPE ENDOSCOPE

(71) Applicant: OLYMPUS CORPORATION, Tokyo (JP)

(72) Inventors: Yuji Sakai, Kodaira (JP); Hiroyuki Takizawa, Chofu (JP); Daiki Ariyoshi, Chofu (JP); Soichiro Koshika, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/412,419

(22) Filed: Jan. 23, 2017

(65) Prior Publication Data
US 2017/0131541 A1 May 11, 2017

Related U.S. Application Data

(63) Continuation of application No. PCT/JP2015/074726, filed on Aug. 31, 2015.

(30) Foreign Application Priority Data

Dec. 25, 2014 (JP) ................................. 2014-263190

(51) Int. Cl.
G02B 6/06 (2006.01)
G02B 26/10 (2006.01)
(Continued)

(52) U.S. Cl.
CPC .......... *G02B 26/103* (2013.01); *A61B 1/0661* (2013.01); *G02B 23/2469* (2013.01)

(58) Field of Classification Search
CPC .............. G02B 26/103; G02B 23/2469; A61B 1/0661; A61B 1/07
(Continued)

(56) References Cited

U.S. PATENT DOCUMENTS 5,097,838 A * 3/1992 Hirooka ............. A61B 1/00098
600/463
6,615,072 B1 * 9/2003 Izatt ..................... A61B 5/0066
600/478

(Continued)

FOREIGN PATENT DOCUMENTS

JP 2002-146498 A 5/2002
JP 2011-139781 A 7/2011
(Continued)

OTHER PUBLICATIONS

International Search Report dated Nov. 24, 2015 issued in PCT/JP2015/074726.
(Continued)

*Primary Examiner* — Ryan Lepisto
*Assistant Examiner* — Guy Anderson
(74) *Attorney, Agent, or Firm* — Scully, Scott, Murphy & Presser, P.C.

(57) ABSTRACT

A scanning type endoscope includes a light guide section configured to guide illumination light, a ferrule provided along the light guide section, an actuator configured to vibrate the ferrule to thereby swing a distal end of the light guide section, a cylindrical member configured to include a space containing the light guide section, the ferrule and the actuator and being provided along the light guide section, and a damping section configured to fix the ferrule to the cylindrical member and absorb vibration of the ferrule, in which the damping section is formed of a ferrule holding member configured to hold a proximal end of the ferrule and a ring-shaped member configured to fix the ferrule holding member to the cylindrical member, be disposed near a joint in the cylindrical member connected to holding member and be made of a material that absorbs vibration of the ferrule.

2 Claims, 7 Drawing Sheets

(51) Int. Cl.
*A61B 1/06* (2006.01)
*G02B 23/24* (2006.01)

(58) Field of Classification Search
USPC .......................................... 385/25, 115–121
See application file for complete search history.

(56) References Cited

U.S. PATENT DOCUMENTS

| | | | | |
|---|---|---|---|---|
| 6,856,712 | B2* | 2/2005 | Fauver | G02B 6/241 385/12 |
| 7,129,472 | B1* | 10/2006 | Okawa | A61B 1/00059 250/216 |
| 8,224,428 | B2* | 7/2012 | Cui | A61B 5/0066 464/174 |
| 9,400,161 | B2* | 7/2016 | Cha | G01B 9/0205 |
| 9,532,766 | B2* | 1/2017 | Vardi | A61B 5/0095 |
| 9,575,034 | B2* | 2/2017 | Rasselkorde | G01N 29/262 |
| 2001/0055462 | A1* | 12/2001 | Seibel | A61B 1/00048 385/147 |
| 2002/0064341 | A1* | 5/2002 | Fauver | G02B 6/241 385/25 |
| 2003/0004412 | A1* | 1/2003 | Izatt | A61B 5/0066 600/425 |
| 2006/0007514 | A1* | 1/2006 | Desai | B82Y 20/00 359/223.1 |
| 2007/0035855 | A1* | 2/2007 | Dickensheets | A61B 5/0068 359/819 |
| 2008/0147000 | A1* | 6/2008 | Seibel | A61M 25/0158 604/98.01 |
| 2008/0218824 | A1* | 9/2008 | Johnston | A61B 5/0059 359/199.1 |
| 2008/0265178 | A1* | 10/2008 | Johnston | G02B 26/10 250/492.1 |
| 2009/0028407 | A1* | 1/2009 | Seibel | A61B 1/0008 382/131 |
| 2009/0189485 | A1* | 7/2009 | Iyoki | B82Y 35/00 310/317 |
| 2009/0218641 | A1* | 9/2009 | Melville | H01L 41/092 257/415 |
| 2009/0323146 | A1* | 12/2009 | Cui | A61B 5/0066 359/200.2 |
| 2010/0121146 | A1* | 5/2010 | Sugimoto | A61B 1/0008 600/117 |
| 2010/0168515 | A1* | 7/2010 | Sugimoto | A61B 1/0008 600/109 |
| 2013/0242069 | A1* | 9/2013 | Kobayashi | A61B 1/00009 348/65 |
| 2014/0300901 | A1* | 10/2014 | Cha | G01B 9/0205 356/479 |
| 2016/0022119 | A1* | 1/2016 | Shahmoon | A61B 1/00096 600/182 |
| 2016/0367109 | A1* | 12/2016 | Imaizumi | A61B 1/04 |

FOREIGN PATENT DOCUMENTS

JP 2013-244045 A 12/2013
WO WO 2014/196258 A1 12/2014

OTHER PUBLICATIONS

Japanese Office Action dated Jul. 26, 2016 issued in JP 2016-520127.

* cited by examiner

SCANNING TYPE ENDOSCOPE

CROSS REFERENCE TO RELATED APPLICATION

This application is a continuation application of PCT/JP2015/074726 filed on Aug. 31, 2015 and claims benefit of Japanese Application No. 2014-263190 filed in Japan on Dec. 25, 2014, the entire contents of which are incorporated herein by this reference.

BACKGROUND OF THE INVENTION

1. Field of the Invention

The present invention relates to a scanning type endoscope configured to scan illumination light to acquire an endoscope image.

2. Description of the Related Art

In recent years, endoscopes configured to scan illumination light have been widely used in a medical field and the like. Scanning type endoscopes are also being proposed which are configured to two-dimensionally scan light guided by a light guide section on an object such as an observation region, and receive and image reflected light.

As a conventional example of such scanning type endoscopes, Japanese Patent Application Laid-Open Publication No. 2011-139781 discloses a confocal optical unit and discloses a structure in which a magnetic drive plate formed of a magnetic member such as silicon steel is attached, through bonding, to a distal end portion of an optical fiber that forms a light guide section in the confocal optical unit, and the magnetic drive plate and the optical fiber are flexibly supported by a flexible support body such as rubber so as not to obstruct a displacement in a Y-axis direction of the distal end of the optical fiber due to a deformation in the Y-axis direction of the magnetic drive plate.

SUMMARY OF THE INVENTION

A scanning type endoscope according to an aspect of the present invention includes a light guide section configured to guide illumination light generated by a light source section and irradiate an object with the illumination light, a ferrule provided along the light guide section, an actuator configured to vibrate the ferrule to swing a distal end of the light guide section to thereby scan the object with the illumination light guided from the light guide section, a cylindrical member configured to hold an optical member that emits the illumination light to scan the object, the illumination light from the light guide section being incident on the optical member, and the distal end of the light guide section being swung by the actuator, the cylindrical member including a space containing the light guide section, the ferrule and the actuator and being provided along the light guide section, and a damping section configured to fix the ferrule to the cylindrical member and absorb vibration of the ferrule at least at a portion contacting the cylindrical member, in which the damping section is formed of a ferrule holding member configured to hold a fixed end which is a proximal end of the ferrule and a ring-shaped member configured to fix the ferrule holding member to the cylindrical member, be disposed near a joint in the cylindrical member connected to at least the ferrule holding member and be made of a material that absorbs vibration of the ferrule.

DETAILED DESCRIPTION OF THE PREFERRED EMBODIMENT(S)

Hereinafter, an embodiment of the present invention will be described with reference to the accompanying drawings.

First Embodiment

Figure 1:
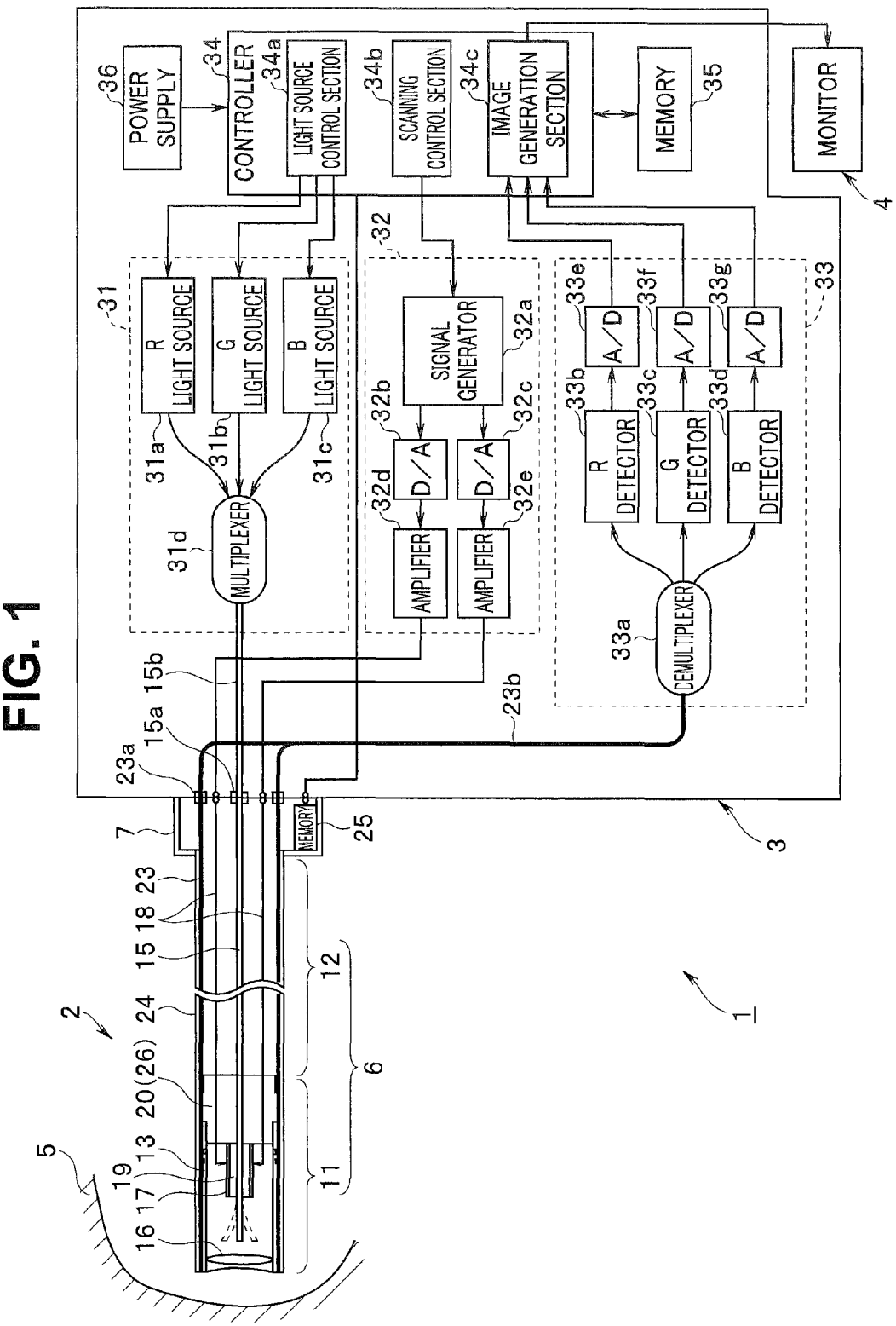
FIG. 1 is a diagram illustrating an overall configuration of a scanning type endoscope apparatus provided with a first embodiment of the present invention.

As shown in FIG. 1, a scanning type endoscope apparatus 1 includes a scanning type endoscope 2 according to a first embodiment of the present invention, a main body (or scanning type endoscope control apparatus) 3 to which the scanning type endoscope 2 is detachably connected and a monitor 4 as a display apparatus connected to the main body 3.

The scanning type endoscope 2 includes an insertion portion 6 formed into an elongated shape and with flexibility to be insertable into a body or a body cavity of a subject 5 and a connector 7 to detachably connect the scanning type endoscope 2 to the main body 3 provided at a proximal end (rear end) of the insertion portion 6.

Furthermore, the insertion portion 6 includes a rigid distal end portion 11 and a flexible tube portion 12 configured to extend from a rear end of the distal end portion 11 toward the connector 7. Note that a freely bendable bending portion may be provided between the distal end portion 11 and the flexible tube portion 12 and an operation portion may be provided between the flexible tube portion 12 and the connector 7, which is provided with an operation knob or the like configured to bend the bending portion.

The distal end portion 11 includes a cylindrical member 13 as a rigid cylindrical member and a rear end of the cylindrical member 13 is connected to a ferrule holding member 20.

An optical fiber 15 configured to form a light guide section that guides illumination light is inserted through the insertion portion 6 and a proximal end (rear end) of the optical fiber 15 is connected to an optical fiber 15b inside the main body 3 (at an optical connection portion 15a of the connector 7). Illumination light generated at a light source unit 31 inside the main body 3 is made incident on a proximal end of the optical fiber 15 via the optical fiber 15b. The illumination light guided by the optical fiber 15 is emitted toward an object such as a region to be inspected in the subject 5 via an illumination lens 16 that forms a condensing optical member attached to a distal end of the cylindrical member 13 opposite to the distal end face from a distal end face of the optical fiber 15.

Figure 2:
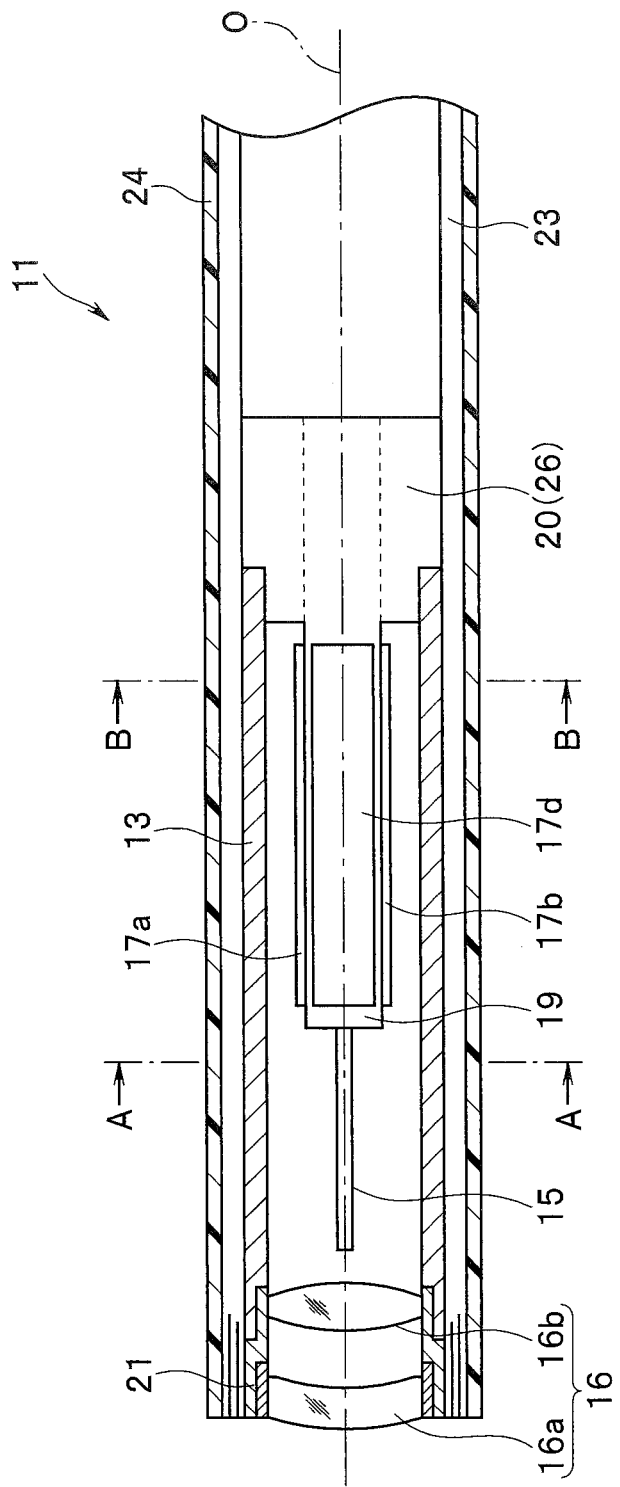
FIG. 2 is a longitudinal cross-sectional view illustrating a structure in the vicinity of a distal end portion of a scanning type endoscope of the first embodiment.

Note that although FIG. 1 shows a structure with the illumination lens 16 forming the optical member directly attached to the distal end of the cylindrical member 13, a structure may also be adopted in which a lens barrel 21 provided with lenses 16a and 16b making up the illumination lens 16 as shown in FIG. 2 is attached to the distal end of the cylindrical member 13. The lens barrel 21 is configured to engage with two lens cylindrical bodies to which the lenses 16a and 16b are attached so as to be movable in an optical axis direction respectively, making it possible to adjust a focal length of the illumination lens 16.

An actuator 17 (shown in FIG. 2 using actuator elements 17a, 17b and 17d that form the actuator 17) that forms a scanning section configured to scan so as to swing the distal end side of the optical fiber 15 in a direction orthogonal to the longitudinal direction of the optical fiber 15 is disposed inside the cylindrical member 13 that forms the distal end portion 11. The actuator 17 is configured to expand/contract by applying a drive signal (or drive voltage) from a drive unit 32 inside the main body 3 via a drive line 18 inserted through the insertion portion 6 and vibrate the distal end side of the optical fiber 15 as the actuator 17 expands/contracts.

The above-described actuator 17 is bonded to a side face of a ferrule 19 interposed between the optical fiber 15 and the actuator 17 as a bonding member or a support member. The ferrule 19 transmits a force corresponding to the expansion/contraction of the actuator 17 to the optical fiber 15. In other words, the actuator 17 vibrates the ferrule 19 to thereby vibrate the distal end side of the optical fiber 15 that forms a light guide section.

Furthermore, a proximal end (rear end) side of the ferrule 19 is held by the ferrule holding member 20 configured to form a ferrule holding section to hold the ferrule 19. Since the actuator 17 is driven with the rear end being held by the ferrule holding member 20, the ferrule holding member 20 is located at a position (in the vicinity) of a fixed end in the vibration by the actuator 17.

The rear end of the cylindrical member 13, for example, engages with an outer circumferential surface near a front end of the ferrule holding member 20 and both members are fixed using an adhesive or the like.

A light-receiving optical fiber bundle (abbreviated as "light-receiving optical fiber") 23 for receiving reflected light of illumination light radiated onto the object is annularly disposed outside the cylindrical member 13 and the ferrule holding member 20.

The light received by the light-receiving optical fiber 23 (return light or reflected light from the object) is guided to a light-receiving optical fiber 23b inside the main body 3 via an optical connection section 23a of the connector 7. The light guided to the light-receiving optical fiber 23b is made incident on a detection unit 33 and converted to an electric signal.

The annularly disposed light-receiving optical fiber 23 is covered and protected with an exterior member 24.

Each scanning type endoscope 2 includes a memory 25 configured to store information such as drive data to cause the actuator 17 to drive the distal end of the optical fiber 15 according to a predetermined scanning pattern and coordinate position data or the like corresponding to an irradiation position when the distal end of the optical fiber 15 is driven. The information stored in the memory 25 is inputted to a controller 34 inside the main body 3 via a contact of the connector 7 and a signal line.

Figure 3A:
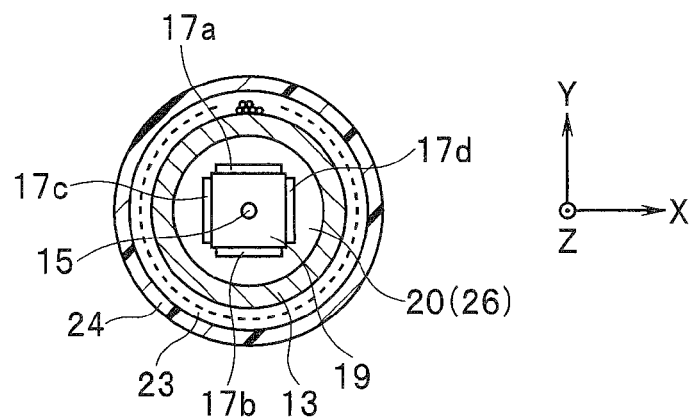
FIG. 3A is a cross-sectional view along a line A-A in FIG. 2.

FIG. 2 illustrates a detailed structure in the vicinity of the distal end portion 11 in FIG. 1. FIG. 3A is a cross-sectional view along a line A-A in FIG. 2 and FIG. 3B is a cross-sectional view along a line B-B in FIG. 2.

As shown in FIG. 2 and FIG. 3A, the ferrule 19 disposed inside the cylindrical member 13 along its central axis O is, for example, a rectangular parallelepiped rigid member, and is formed of, for example, zirconia (ceramic) or nickel.

Figure 3B:
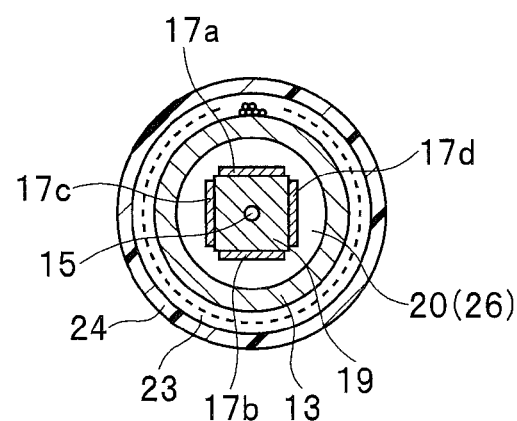
FIG. 3B is a cross-sectional view along a line B-B in FIG. 2.

As shown in the lateral cross section in FIG. 3B, the ferrule 19 is formed into a square quadrangular prism shape, the optical fiber 15 passing through a hole along the central axis O is fixed and the actuator elements 17a and 17b, and 17c and 17d making up the actuator 17 are attached to both side faces in the Y-axis direction (up-down direction of the sheet) and both side faces in the X-axis direction (left-right direction of the sheet) respectively.

Each actuator element is made up of a piezoelectric element such as PZT (lead zirconate titanate) and expands/contracts in the longitudinal direction (Z-axis direction in FIG. 3A) by an application of a drive signal. Therefore, by applying a drive signal in an opposite phase to, for example, the actuator elements 17a and 17b (to cause one of the actuator elements 17a and 17b to expand and the other to contract) with the proximal end being held or fixed, it is possible to vibrate the distal end side of the optical fiber 15 in an up-down direction as shown by a dotted line in FIG. 1.

Figure 4:
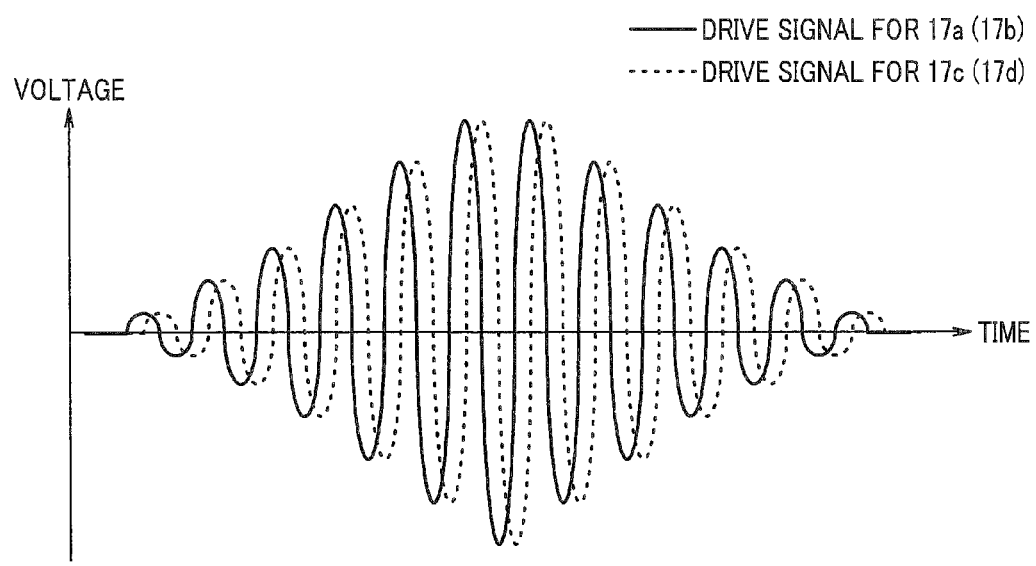
FIG. 4 is a diagram illustrating a voltage waveform of a drive signal applied to an actuator element.
Figure 5:
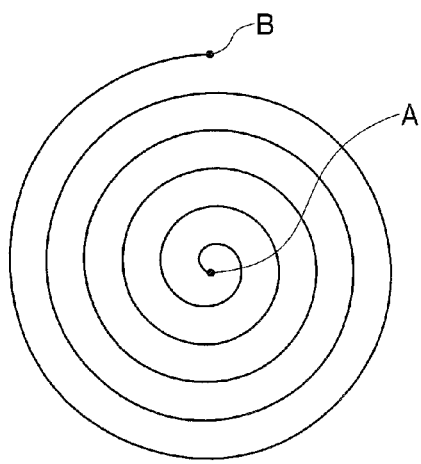
FIG. 5 is a diagram illustrating a spiral-shaped track scanned by a distal end of an optical fiber when the drive signal in FIG. 4 is applied.

Actually, two drive signals having a phase difference of 90° are used as drive signals to be applied to the actuator elements 17a and 17b, and 17c and 17d as shown in FIG. 4. By applying two drive signals having a phase difference of 90°, the distal end side of the optical fiber 15 scans in a circular shape, and by changing the value (amplitude) of the drive voltage so as to continuously increase, the distal end side of the optical fiber 15 describes a track scanning spirally from a position A which becomes a scanning starting point in the center to a position B as shown in FIG. 5. After scanning up to the position B, the distal end returns to the position A which is the scanning starting point by continuously decreasing the drive voltage (the spiral track returning from the position B to the position A is not shown in FIG. 5).

As shown by a dotted line in FIG. 2, the rear end of the ferrule 19 is fitted into a hole (whose lateral cross section has a square shape) of the ferrule holding member 20 and is fixed to the ferrule holding member 20 using an adhesive or the like. The ferrule holding member 20 is formed of a columnar shaped rigid member provided with a hole for fixing the ferrule 19 on the center side as described above.

Furthermore, a stepped portion having a radius which is smaller by a value corresponding to a thickness of the cylindrical member 13 is provided on a front end side of the ferrule holding member 20, this stepped portion is fitted into the rear end of the cylindrical member 13, and both members (the ferrule holding member 20 and the cylindrical member 13) are fixed using an adhesive or the like.

In the present embodiment, a damping section disposed at least in the vicinity of a joint connecting the cylindrical member 13 and the ferrule holding member 20 and made of a material that absorbs vibration of the ferrule 19 is formed of the ferrule holding member 20 which is formed using a damping member 26 made of an twin crystal type damping alloy having a vibration absorbing characteristic or function.

The above-described twin crystal type damping alloy is made up of an aggregate of twin crystal crystalline structure, and when vibration that forms vibration energy is applied from outside, friction is produced between twin crystals and the vibration energy is converted to thermal energy by friction. In other words, when vibration is applied, the ferrule holding member 20 formed of the damping member 26 efficiently absorbs the vibration and efficiently damps the vibration.

Since the present embodiment has a structure in which when the distal end of the optical fiber 15 that forms the light guide section is vibrated by driving the actuator 17, the vibration is transmitted to the optical fiber 15 by vibrating the ferrule 19, it is possible to efficiently absorb vibration at a fixed end of the ferrule 19 by holding the proximal end of the ferrule 19 (which becomes the fixed end of the ferrule 19) and forming the ferrule holding member 20 itself fixed (connected) to the cylindrical member 13 using the damping member 26.

As shown in FIG. 1, the main body 3 includes the light source unit 31, the drive unit 32, the detection unit 33, the controller 34 configured to control each unit of the main body 3, a memory 35 connected to the controller 34 and configured to store various types of information and a power supply (circuit) 36 configured to supply DC power to the controller 34 or the like.

The light source unit 31 includes an R light source 31a configured to generate light of red wavelength band (also referred to as "R light"), a G light source 31b configured to generate light of green wavelength band (also referred to as "G light"), a B light source 31c configured to generate light of blue wavelength band (also referred to as "B light"), and a multiplexer 31d configured to multiplex (mix) R light, G light and B light.

The R light source 31a, the G light source 31b and the B light source 31c are configured using, for example, laser light sources and emit, when turned ON under the control of the controller 34, R light, G light and B light to multiplexer 31d respectively. The controller 34 includes a light source control section 34a made up of a central processing unit (abbreviated as "CPU") configured to control discrete light emissions of the R light source 31a, the G light source 31b and the B light source 31c.

The light source control section 34a of the controller 34 sends control signals to the R light source 31a, the G light source 31b and the B light source 31c to cause them to simultaneously emit light pulses and the R light source 31a, the G light source 31b and the B light source 31c simultaneously generate R light, G light and B light and emit the light to the multiplexer 31d.

The multiplexer 31d multiplexes the R light from the R light source 31a, the G light from the light source 31b and the B light from the light source 31c, supplies the multiplexed light to a light incident surface of the optical fiber 15b and the optical fiber 15b supplies the multiplexed R light, G light and B light to the optical fiber 15 as illumination light.

The drive unit 32 includes a signal generator 32a, D/A converters 32b and 32c and amplifiers 32d and 32e.

The signal generator 32a generates a signal to drive a light emission end portion at the distal end of the optical fiber 15 so as to describe a spiral track based on the control of a scanning control section (or drive control section) 34b of the controller 34 and outputs the signal to the D/A converters 32b and 32c. The D/A converters 32b and 32c convert digital signals outputted from the signal generator 32a to analog signals and output the analog signals to the amplifiers 32d and 32e respectively.

The amplifiers 32d and 32e amplify the signals outputted from the D/A converters 32b and 32c respectively and output drive signals having the waveforms shown in FIG. 4 to the actuator 17.

The distal end of the optical fiber 15 is vibrated so as to form a spiral scanning track as shown in FIG. 5.

The detection unit 33 includes a demultiplexer 33a, detectors 33b, 33c and 33d, and A/D converters 33e, 33f and 33g.

The demultiplexer 33a includes a dichroic mirror or the like, separates return light emitted from a light emission end face of the light-receiving optical fiber 23b into light beams of R (red), G (green) and B (blue) color components and emit the separated light beams to the detectors 33b, 33c and 33d.

The detectors 33b, 33c and 33d are made up of photodetectors such as photodiodes, detect intensity of the R light, intensity of the G light and intensity of the B light outputted from the demultiplexer 33a respectively, generate analog R, G and B detection signals corresponding to the detected intensities of the R light, the G light and the B light and output the detection signals to the A/D converters 33e, 33f and 33g respectively.

The A/D converters 33e, 33f and 33g convert the analog R, G and B detection signals outputted from the detectors 33b, 33c and 33d to digital R, G and B detection signals respectively and output the detection signals to an image generation section 34c configured to generate images in the controller 34.

The memory 35 stores a control program or the like to control the main body 3 in advance. The memory 35 stores information on coordinate positions read from the memory 25 by the controller 34 of the main body 3.

The controller 34 is configured using a central processing unit (abbreviated as "CPU"), reads the control program stored in the memory 35 and controls the light source unit 31 and the drive unit 32 based on the read control program.

The scanning type endoscope 2 of the present embodiment holds the optical fiber 15 configured to guide illumination light generated by the light source unit 31 that forms a light source section and form a light guide section that irradiates an object with the illumination light, the ferrule 19 provided along the light guide section, the actuator 17 configured to drive the distal end of the light guide section by vibrating the ferrule 19 to scan the illumination light guided from the light guide section on the object, and the illumination lens 16 that forms an optical member configured to receive the illumination light from the light guide section, the distal end of which is driven by the actuator 17, and thereby emit the illumination light to be scanned on the object, includes a space containing the light guide section, the ferrule 19 and the actuator 17, fixes the ferrule 19 to the cylindrical member 13 (and the lens barrel 21) that forms a cylindrical member provided along the light guide section and the cylindrical member and includes the damping member 26 made of a twin crystal type damping alloy or the like that forms a damping section that absorbs vibration of the ferrule 19.

Next, operation of the present embodiment will be described.

As shown in FIG. 1, the scanning type endoscope 2 is connected to the main body 3, a power switch, which is not shown, of the main body 3 is turned ON to bring the scanning type endoscope apparatus 1 into an operation state. In the operation state, the controller 34 reads information of the memory 25 and stores the information in the memory 35. Furthermore, the scanning control section 34b of the controller 34 performs control so as to apply a drive signal from the drive unit 32 to the actuator 17. With the application of the drive signal, the actuator 17 spirally scans (swings) the distal end side of the optical fiber 15 from the scan starting position A to the scan ending position B shown in FIG. 5.

Furthermore, the light source control section 34a of the controller 34 controls the light source unit 31 to discretely and sequentially emit light pulses at predetermined coordinate positions set in advance. Furthermore, the detection unit 33 sequentially samples return light from the subject 5 side when light pulses are discretely emitted to acquire a detection signal. The detection unit 33 sends the acquired detection signal to the image generation section 34c and the image generation section 34c temporarily stores the inputted detection signal in, for example, the memory 35.

The image generation section 34c of the controller 34 converts image information made up of the detection signal stored in the memory 35 and position information of pulse emission when the detection signal is acquired to a standard image signal in a case of raster scanning and outputs the image signal to the monitor 4. The image generation section 34c causes the monitor 4 to display an image by return light when spiral scanning is performed as an endoscope image.

The endoscope image displayed on the monitor 4 is an image acquired when the optical fiber 15 that forms a light guide section disposed along the central axis O of the cylindrical member 13 is held by the ferrule 19, the actuator 17 is attached to upper, lower, left and right side faces of the ferrule 19, the proximal end portion of the actuator 17 is held by the ferrule holding member 20, and the distal end of the optical fiber 15 is swung by the actuator 17 in the X-axis and Y-axis directions which are directions orthogonal to the central axis O.

As described above, when the distal end of the optical fiber 15 is spirally scanned (swung) by the actuator 17, it is preferable to hold the ferrule holding member 20 that holds the proximal end portion of the ferrule 19 and the illumination lens 16 held (fixed) to the distal end side of the cylindrical member 13 so as not to swing for a period during which images for one frame are generated (that is, a period during which scanning is performed from the position A to the position B) to acquire images of good image quality.

When the distal end of the optical fiber 15 is swung (scanned) by the actuator 17, since the actuator 17 fixes the proximal end side of the attached ferrule 19 to the rear end of the cylindrical member 13 by the ferrule holding member 20, vibration caused by swinging by the actuator 17 may also be transmitted to the ferrule holding member 20 via the fixed part and the vibration may be further transmitted from the proximal end of the cylindrical member 13 to the part holding the illumination lens 16 on the distal end side, possibly causing the illumination lens 16 to vibrate.

In the present embodiment, since the ferrule holding member 20 itself is formed of the damping member 26, even in an operating environment in which the actuator 17 is caused to be substantially vibrated by a drive signal, having such an influence as to cause the ferrule holding member 20 to vibrate, the damping member 26 can absorb the vibration, and thereby prevent the image quality from degrading.

Furthermore, since the ferrule holding member 20 is structured to be fixed by being coupled (or connected) with the proximal end of the cylindrical member 13 as a cylindrical member to hold the illumination lens 16 as an optical member on the distal end side directly or via the lens barrel 21, even if vibration occurs on the cylindrical member 13 side, the damping member 26 that forms the ferrule holding member 20 can absorb the vibration and prevent degradation of image quality.

Therefore, according to the present embodiment, it is possible to absorb vibration which is likely to occur around a portion connecting (coupling) the ferrule holding member 20 that forms a portion that holds the proximal end side of the ferrule 19 and the cylindrical member 13 as a cylindrical member that holds the illumination lens 16 as an optical member on the distal end side directly or via the lens barrel 21.

Figure 6:
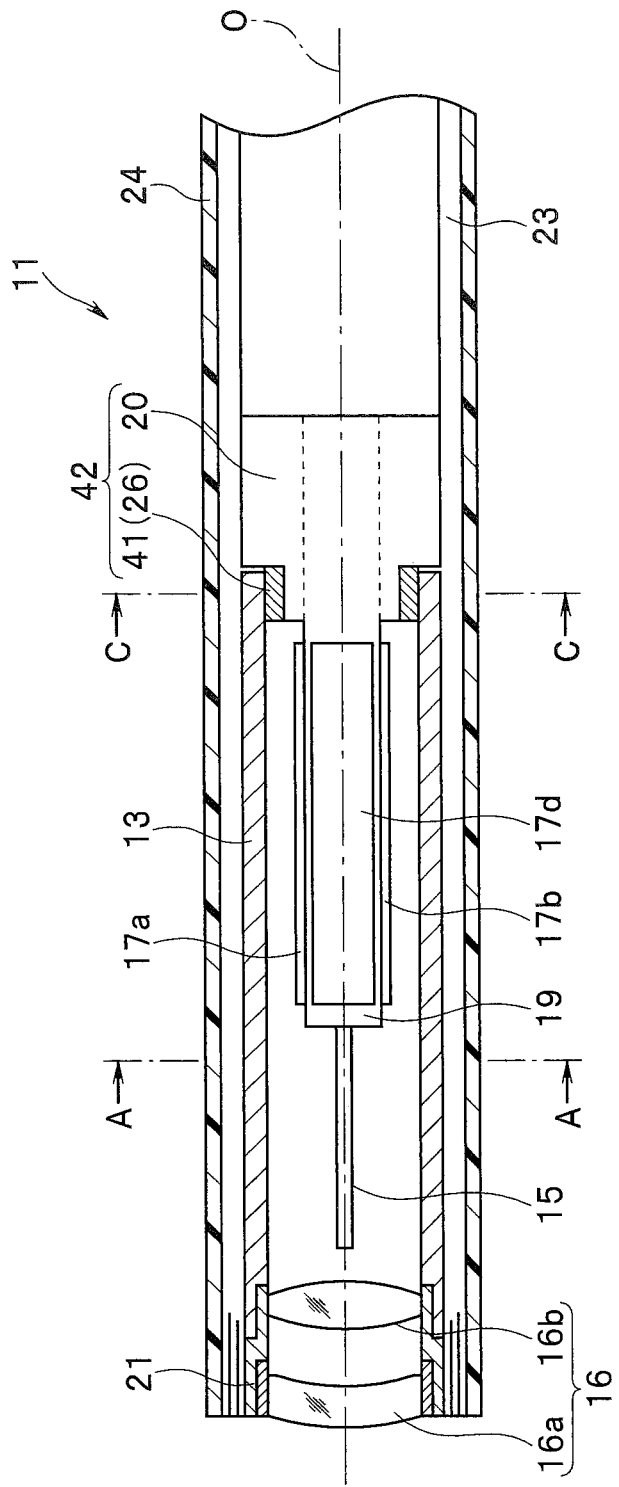
FIG. 6 is a longitudinal cross-sectional view illustrating a structure in the vicinity of a distal end portion of a scanning type endoscope according to a first modification of the first embodiment.

Next, a modification of the first embodiment will be described. FIG. 6 illustrates a structure in the vicinity of a distal end portion according to a modification of the first embodiment. In the first embodiment, the ferrule holding member 20 itself that holds the ferrule 19 provided with the actuator 17 and fixes the illumination lens 16 on the distal end side to the rear end of the cylindrical member 13 that holds the illumination lens 16 via the lens barrel 21 (or without the lens barrel 21) is formed using the damping member 26.

Figure 7:
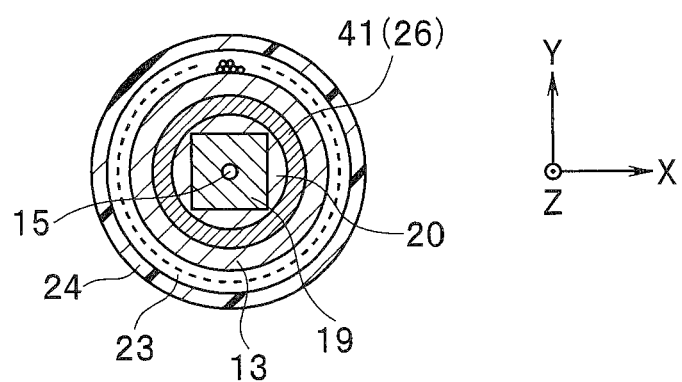
FIG. 7 is a cross-sectional view along a line C-C in FIG. 6.

In contrast, as shown in FIG. 6, the present modification provides a connection member 41 as a ring-shaped member formed of the damping member 26 made of a twin crystal type damping alloy or the like in the portion where the ferrule holding member 20 is fixed to the cylindrical member 13. In the present modification, a damping section 42 is formed of the ferrule holding member 20 to (hold the proximal end of the ferrule 19 and) fix the ferrule 19 to the cylindrical member 13 and the connection member 41 disposed in the vicinity of a joint where the cylindrical member 13 is fixed to the ferrule holding member 20, formed of the damping member 26 as a ring-shaped member to absorb vibration of the ferrule 19. As shown in FIG. 7 as a cross-sectional view along a line C-C in FIG. 6, a configuration is adopted in which while the ring-shaped connection member 41 is inserted, a stepped surface between the rear end of the cylindrical member 13 outside and the ferrule holding member 20 is fixed. Note that the cross section along the line A-A in FIG. 6 is the same as that in FIG. 3A.

In the present modification, the ferrule holding member 20 is formed of a rigid material such as stainless steel or aluminum (alloy). Note that as a further modification, the ferrule holding member 20 may also be formed of the damping member 26.

The rest of the configuration is similar to the configuration of the first embodiment. In the present modification, when an image is acquired through scanning by the scanning type endoscope 2 at the distal end portion 11, if vibration occurs which may cause degradation of image quality, (the damping member 26 of) the connection member 41 formed of the damping member 26 substantially making up the damping section 42 can absorb or reduce the vibration.

For example, when vibration occurs on the cylindrical member 13 side, the vibration propagates to the ferrule holding member 20 via the connection member 41, but in that case, the vibration can be absorbed or reduced by the damping member 26 forming the connection member 41. Even when vibration occurs on the ferrule holding member 20 side or when vibration propagates to the cylindrical member 13 via the connection member 41, the vibration can be likewise absorbed or reduced by the damping member 26. The present modification has substantially the same effects as those of the first embodiment and can form only the small-sized connection member 41 using the damping member 26, and thereby achieve a cost reduction.

Figure 8:
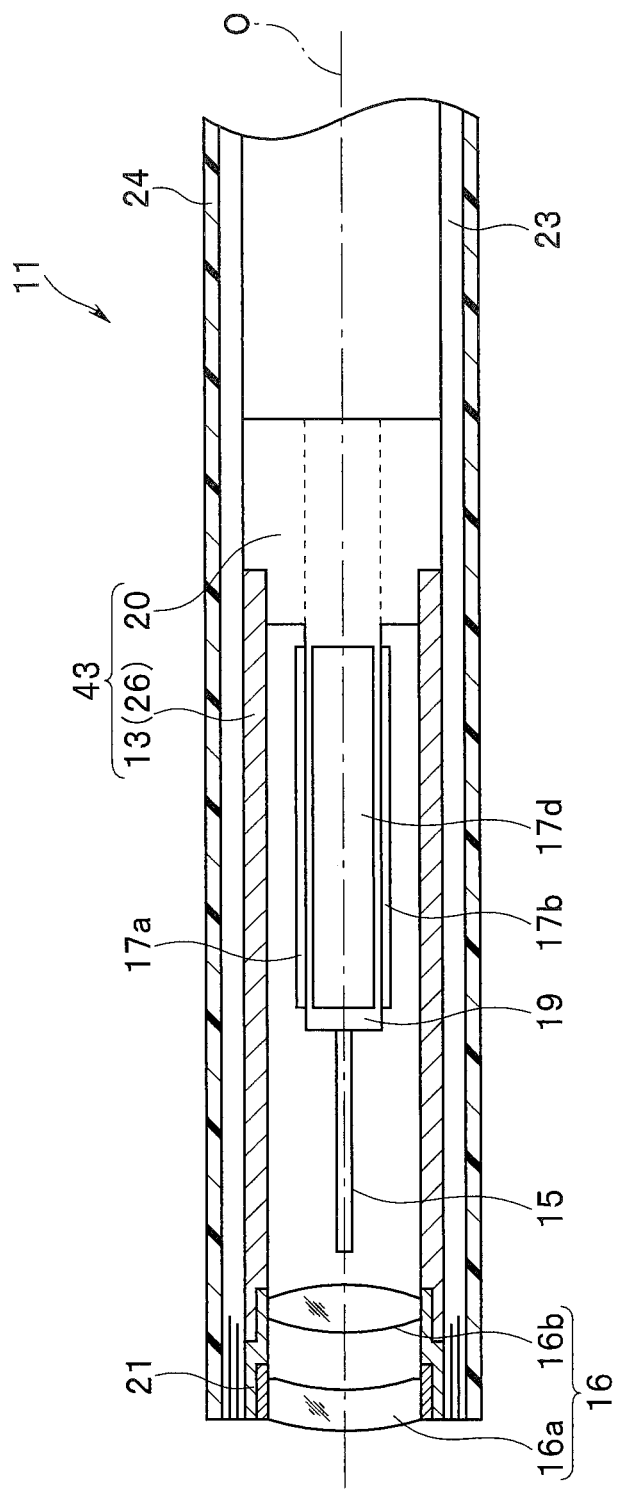
FIG. 8 is a longitudinal cross-sectional view illustrating a structure in the vicinity of a distal end portion of a scanning type endoscope according to a second modification of the first embodiment.

Next, a second modification of the first embodiment will be described. FIG. 8 illustrates a structure in the vicinity of a distal end portion of a scanning type endoscope according to a second modification.

In the present modification, as shown in FIG. 8, the cylindrical member 13 is configured using the damping member 26. In the configuration shown in FIG. 8, the ferrule holding member 20 shown in FIG. 2 in the first embodiment is not configured using the damping member 26 and the cylindrical member 13 is configured using the damping member 26 instead. In this case, the damping member 26 that forms the ferrule holding member 20 in FIG. 2 is substituted by the cylindrical member 13. The rest of the configuration is similar to that described in the first embodiment. Thus, in the present modification, a damping section 43 is formed of the ferrule holding member 20 that holds the proximal end of the ferrule 19 and the cylindrical member 13 formed of the damping member 26 made of a twin crystal type damping alloy or the like that absorbs vibration in the ferrule 19 or the like.

Effects in the present modification are substantially the same as those of the first embodiment. In the present modification, when vibration occurs on the distal end side of the cylindrical member 13, the distal end side portion of the damping member 26 that forms the cylindrical member 13 can absorb or reduce the vibration (in the vicinity of the source of occurrence of the vibration).

Furthermore, in the present modification, since substantially the overall length in the longitudinal direction of the distal end portion 11 is formed of the cylindrical member 13 formed of the damping member 26, even when such external disturbance that vibrates the distal end portion 11 may be added to the optical fiber 15 and the actuator 17 disposed inside the distal end portion 11 from outside the distal end portion 11, it is possible to reduce the influences. In the second modification, the ferrule holding member 20 may also be configured using the damping member 26.

Note that the first embodiment may be combined with the aforementioned modifications or the like. For example, the first embodiment may be combined with the second modification. Furthermore, as a configuration similar to the first modification, for example, a partial peripheral part fixed to the proximal end of the cylindrical member 13 in the ferrule holding member 20 may be formed of the damping member 26 or a structure may be adopted in which a part that becomes the proximal end side of the cylindrical member 13 is formed of the damping member 26 and the portion formed of the damping member 26 is fixed to the ferrule holding member 20.

What is claimed is:

1. A scanning type endoscope comprising:
a light guide section configured to guide illumination light generated by a light source section and irradiate an object with the illumination light;
a ferrule provided along the light guide section;
an actuator configured to vibrate the ferrule to swing a distal end of the light guide section to thereby scan the object with the illumination light guided from the light guide section;
a cylindrical member configured to hold an optical member that emits the illumination light to scan the object, the illumination light from the light guide section being incident on the optical member, and the distal end of the light guide section being swung by the actuator, the cylindrical member including a space containing the light guide section, the ferrule and the actuator and being provided along the light guide section; and
a damping section configured to fix the ferrule to the cylindrical member and absorb vibration of the ferrule at least at a portion contacting the cylindrical member,
wherein the damping section is formed of a ferrule holding member configured to hold a fixed end which is a proximal end of the ferrule and a ring-shaped member configured to fix the ferrule holding member to the cylindrical member, the damping section being disposed near a joint in the cylindrical member connected to at least the ferrule holding member and the damping section being made of a material that absorbs vibration of the ferrule;
wherein the damping section is formed using a twin crystal type damping alloy.

2. The scanning type endoscope according to claim 1, wherein a distal end of the cylindrical member holds the optical member, and
a rear end of the cylindrical member is fixed to a stepped surface of the ferrule holding member via the ring-shaped member.

* * * * *